United States Patent
Suzuki et al.

(10) Patent No.: US 6,821,012 B2
(45) Date of Patent: *Nov. 23, 2004

(54) VACUUM ASSISTED MIXER FOR CAPSULE OF DENTAL RESTORATION MATERIAL

(75) Inventors: Yoshimasa Suzuki, Itabashi-ku (JP); Shuji Aoyagi, Itabashi-ku (JP); Masaaki Kaneko, Itabashi-ku (JP); Yoshihisa Mukasa, Itabashi-ku (JP)

(73) Assignee: GC Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/754,699

(22) Filed: Jan. 12, 2004

(65) Prior Publication Data

US 2004/0141408 A1 Jul. 22, 2004

Related U.S. Application Data

(63) Continuation of application No. 09/852,210, filed on May 10, 2001, now Pat. No. 6,776,516.

(30) Foreign Application Priority Data

May 31, 2000 (JP) ........................................ 2000-163593

(51) Int. Cl.[7] ............................ B01F 11/00; B01F 13/06
(52) U.S. Cl. ........................................ 366/139; 366/602
(58) Field of Search ................................ 366/110, 111, 366/114, 139, 209, 602; 433/90, 91

(56) References Cited

U.S. PATENT DOCUMENTS

| | | |
|---|---|---|
| 3,559,961 A | 2/1971 | Bergendal |
| 4,071,338 A | 1/1978 | Hutter, III et al. |
| 4,197,646 A | 4/1980 | Morrison |
| 4,199,866 A | 4/1980 | Drury |
| 4,871,261 A | 10/1989 | Randklev |
| 5,636,921 A | 6/1997 | Murata et al. |
| 6,152,593 A | 11/2000 | Schaefer et al. |
| 6,355,585 B1 * | 3/2002 | Suzuki et al. .................. 501/35 |
| 6,386,872 B1 * | 5/2002 | Mukasa et al. ............... 433/90 |
| 6,733,170 B2 * | 5/2004 | Mukasa et al. ............. 366/139 |
| 6,776,516 B2 * | 8/2004 | Suzuki et al. ............... 366/139 |
| 2001/0053511 A1 | 12/2001 | Aoyagi et al. |

FOREIGN PATENT DOCUMENTS

| | | |
|---|---|---|
| FR | 2 533 820 A1 | 4/1984 |
| FR | 2 636 834 A1 | 3/1990 |

* cited by examiner

*Primary Examiner*—Charles E. Cooley
(74) *Attorney, Agent, or Firm*—Oblon, Spivak, McClelland, Maier & Neustadt, P.C.

(57) ABSTRACT

There is provided a mixer for a capsule for dental restoration material used for mixing a powder component and a liquid component in a capsule accommodating therein the powder component and the liquid component for restoration of a tooth in the dental remedy field, by rendering a mixing compartment in vacuo so as to make it in a good state where the mixture does not substantially contain air bubbles. The mixer of the present invention has the mixer for a capsule for dental restoration material provided with a capsule holding chamber of holding a mixer for a capsule to shake the capsule accommodating a powder component and a liquid component isolated from the powder component within a cylindrical mixing compartment having an air-permeable filter which can ventilate air outside, placed as an outer wall constituting at least a part of a peripheral wall of the mixing compartment, in a portion other than a portion corresponding to the air-permeable filter, and the capsule holding chamber is connected to a vacuum device.

6 Claims, 5 Drawing Sheets

VACUUM ASSISTED MIXER FOR CAPSULE OF DENTAL RESTORATION MATERIAL

CROSS-REFERENCE TO RELATED APPLICATIONS

The present application is a continuation of U.S. patent application Ser. No. 09/852,210 filed on May 10, 2001 now U.S. Pat. No. 6,776,516, and in turn claims priority to Japanese patent application 2000-163593 filed on May 31, 2000, the entire contents of each of which are hereby incorporated herein by reference.

BACKGROUND OF THE INVENTION

1. Field of the Invention

The present invention relates to a mixer for a capsule for dental restoration material, which is used for mixing a powder component and a liquid component in a capsule for dental restoration material accommodating therein two components of definite amount of the powder component and the liquid component as previously weighed separately, each constituting a dental restoration material to be used in filling, cementing, lining and other applications for restoration of a tooth in the dental remedy field, by rendering a mixing compartment in vacuo so that the mixture may not substantially contain air bubbles therein.

2. Description of the Related Art

In general, a dental restoration material is used for restoration of a tooth, such as filling, cementing and lining. As the dental restoration material, a two-component system material comprising a powder component and a liquid component, which are reacted with each other upon mixing, is usually used. Hitherto, this two-component system dental restoration material was provided for use after appropriately weighing the powder component and the liquid component and mixing them with each other. However, in recent years, for the purposes of omitting a weighing operation of the powder component and the liquid component and an operation for accommodating the dental restoration material after mixing in a syringe for administering it to a site to be restored, there have been developed capsules for dental restoration material, in which definite amounts of the powder component and the liquid component are previously weighed and accommodated separately from each other, the isolated state is released at a desired time, the both components are mixed with each other by mechanical shaking in a mixer, and the resulting mixture is extruded and administered directly to a site to be restored, such as a tooth cavity, through a nozzle.

For example, in a capsule as disclosed in Japanese Patent Publication No. 38853/1991, a powder component of the two components is accommodated in a mixing compartment of a capsule main body, and the other liquid component is charged in a bag (pillow) formed by a sheet film, which is mounted on a side portion of the mixing compartment accommodating the powder component by means of a clip. The capsule main body has an outlet hole in a front end portion thereof. This outlet hole can be clogged in a cylindrical bearing portion in a rear end portion of a nozzle. Further, the nozzle is kept from the outside by means of a separately formed cap, thereby preventing the powder component from leakage out of the mixing compartment. And, when in use, the clip is pushed toward direction of the mixing compartment, thereby smashing and breaking the pillow accommodating the liquid component therein; the liquid component is made to flow into an interior of the mixing compartment through an aperture provided on a side wall of the mixing compartment, followed by shaking in a mixer to mix the liquid component and the powder component with each other; the cylindrical bearing portion in the rear end portion of the nozzle is then rotated to release a passage of the nozzle; and a plunger is pushed by means of a push rod of a separately prepared applier to extrude the mixture through the nozzle.

Further, a two-component system capsule for mixing and discharging as disclosed in Japanese Patent Laid-Open No. 268555/1987 has a bag (pillow) in which a powder component of two components is accommodated in a mixing compartment within a capsule main body, and the other liquid component is accommodated in a bag (pillow) formed by a sheet film comprising a resin, a metal foil, or a laminate comprising a resin and a metal foil. In this pillow, the strength in the main body side is previously set to be low, and the pillow is attached by a cap to be screwed on the container main body in the front end side of the container main body. In use, when the cap is firmly screwed on the capsule main body and moved, the pillow is ruptured, the sheet in the capsule main body side is broken, and the liquid component flows into the mixing compartment through an outlet hole provided on a center axis of the front end of the capsule main body. Thus, when shaking is performed in a mixer, the liquid component is mixed with the powder component. After mixing, a through rod set within a nozzle provided on a center axis of the cap is pushed in and breaks through the sheet of the pillow on the cap side, i.e., on the nozzle side, to form a discharge outlet for the mixture. Thereafter, the through rod is removed, a plunger set in the interior of the rear end portion of the capsule main body is moved towards the side of the front end portion of the capsule main body by a push rod of an applier, and the mixture in the mixing compartment is discharged through the nozzle.

Further, like Japanese Patent Laid-Open No. 268555/1987 as cited above, Japanese Patent Publication No. 81384/1991 discloses a capsule for dental restoration material in which a bag (pillow) having a liquid component accommodated therein, which is formed by a sheet film such as an aluminum foil, is provided on the outside of a front end of a mixing compartment of a capsule main body; and the pillow is ruptured by screwing and pressing a cap, thereby making the liquid component flow into the mixing compartment through an outlet hole on a center axis of the capsule main body. Thus, when a mixer is shaken, the liquid component is mixed with the powder component. Thereafter, a pillow breakthrough body-equipped plunger provided in a rear end portion of the capsule main body is moved by means of a push rod of an applier, to break through a front end of the pillow on the nozzle side, thereby extruding the mixture in the mixing compartment.

Each of the above-described capsules used a pillow in which the liquid component is wrapped by a sheet film using a metal foil or the like. Thus, as a capsule not using such a pillow, Japanese Patent Laid-Open No. 131459/1996 proposes a capsule having a structure comprising a cylindrical capsule main body having a mixing compartment for accommodating a powder component therein, in which a thin film-like seal portion for clogging a circular outlet hole for mixture, which is provided on a center axis of a front end portion, is formed, male screw is provided on an outer periphery side surface from the front end portion to a center portion, and an applier-engaging groove is formed on an outer periphery side surface in the vicinity of a rear end portion; a cup-like liquid-accommodating tool for accommodating a liquid component therein, in which a thin film-like seal portion forming a circular flow-in hole for the liquid component is formed on a center axis of a front end portion thereof, an evagination portion that is embedded in a cylindrical portion for forming the mixing compartment of the capsule main body is provided on an outer periphery surface in the vicinity of the front end portion, and a convex stopper having a size such that it does not easily slide into the capsule main body during breaking through the thin film-like seal portion to form the flow-in hole for the liquid component, however, when a large force is applied, it the stopper not inhibited to slide into the capsule main body, is provided on an outer side surface in the vicinity of a rear end portion thereof; a plunger, in which a tip portion thereof for breaking through the thin film-like seal portion of the liquid-accommodating tool and the thin film-like seal portion of the capsule main body has a planar rod-like protrusion in its front end portion, and an evagination portion that is engaged with a cylindrical portion within the liquid-accommodating tool is provided on an outer periphery surface in the vicinity of the front end portion; a cap having a nozzle-engaging mouth on a center axis of a front end portion thereof and screw provided, on an inner periphery side surface thereof with a female screw to be screw engaged with the male screw that is a screw provided on the capsule main body; and a nozzle having a shape such that a rear end portion thereof can be engaged with the outer surface of the front end portion of the capsule main body.

In the capsules having such various structures, when the dental restoration material comprising two components of definite amounts of the previously weighed powder component and liquid component as is mixed by shaking in a mixer, air present in the mixing compartment mingles into the mixture to stay therein. For this reason, the dental restoration material administered in a restoration site such as a cavity of a tooth contains the air bubbles. Accordingly, the capsules of the related art involved various problems including reduction in the strength and a change in the color tone with respect to the dental restoration material.

Thus, in order to overcome the above problems of the capsules for dental restoration material of the related art and to provide a capsule for dental restoration material, which is free from the occurrence of a phenomenon wherein, when a dental restoration material of the related art comprising two components of definite amounts of previously weighed powder component and liquid component accommodated in a capsule for dental restoration material is mixed, air present in a mixing compartment mingles as air bubbles into the mixture, we, the present inventors proposed in Japanese Patent Application No. 2000-163408 a capsule for dental restoration material having an air-permeable filter that does not allow to pass the powder component and the liquid component therethrough but can ventilate air within the mixing compartment outside of the mixing compartment placed at least in a part of a peripheral wall of the mixing compartment.

SUMMARY OF THE INVENTION

An object of the present invention is to provide a mixer for a capsule for dental restoration material, in which air present in the compartment for mixing the dental restoration material comprising two components of the powder component and the liquid component accommodated in the capsule for dental restoration material as proposed above by the inventors is sucked out of the mixing compartment to render the mixing compartment in vacuo, whereby the powder component and the liquid component can be mixed with each other by shaking.

In order to achieve the above-described object, the present inventors made extensive and intensive investigations. As a result, it has been found that the object can be achieved by a mixer for a capsule for dental restoration material for mixing a powder component and a liquid component of a dental restoration material by shaking within a mixing compartment of a capsule for dental restoration material having an air-permeable filter which can ventilate air within the mixing compartment into the outside of the mixing compartment, the filter constituting as an outer wall at least a part of a peripheral wall of the mixing compartment, wherein the mixer is provided with a capsule holding chamber for holding the capsule for dental restoration material in a portion other than a portion corresponding to the air-permeable filter, and the capsule holding chamber is connected to a vacuum device, leading to accomplishment of the present invention.

Further, it has also been found that when, in the mixer for a capsule for dental restoration material, the vacuum device is an ejector to be connected to a compressed air supply device for a dental unit, a compressed air supply device for a dental unit placed in a dental clinic can be used as a power source thereof, and hence, the system can be made at low cost and of simple structure.

Figure 1:
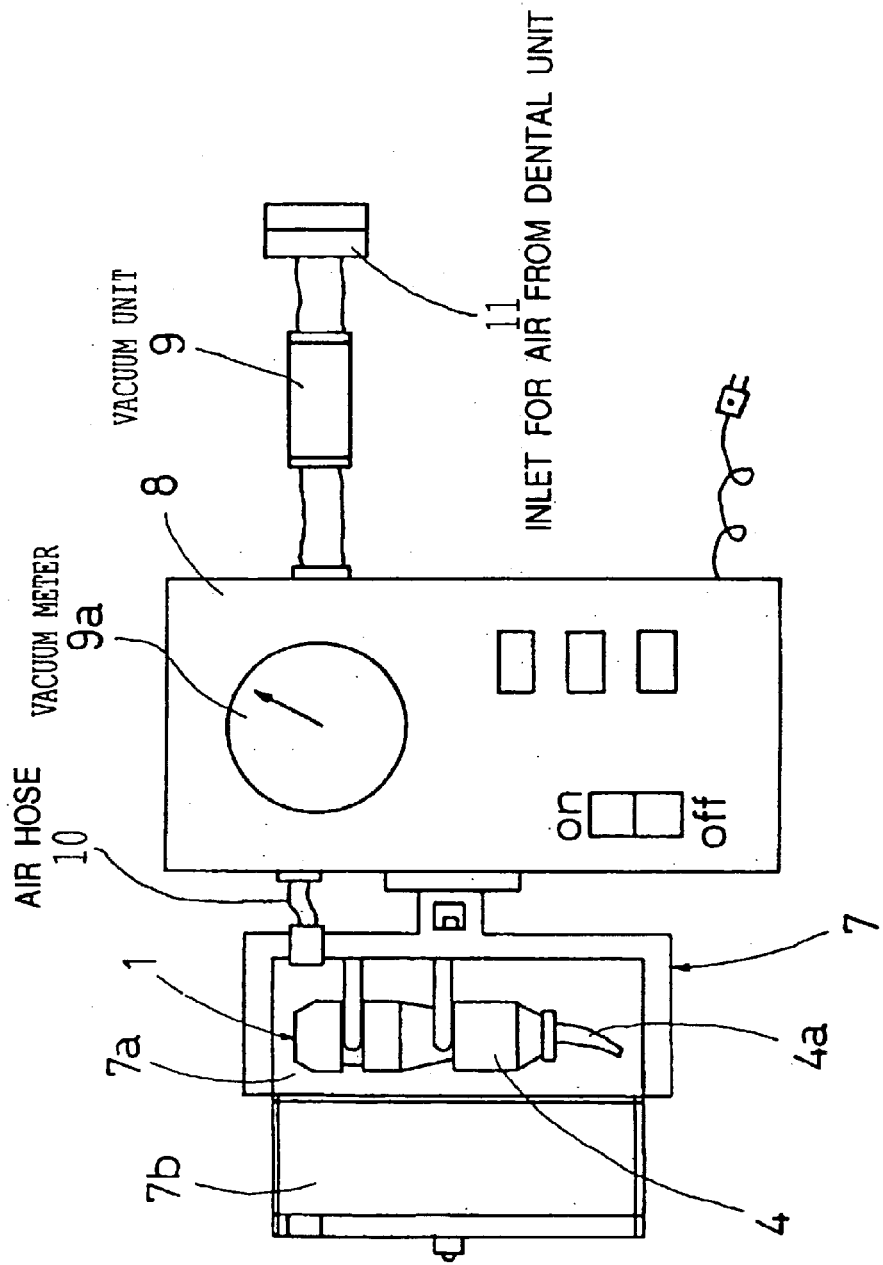
FIG. 1 is an explanatory view schematically showing a structure of a mixer for a capsule for dental restoration material according to the present invention.

First of all, the capsule for dental restoration material used in the mixer for a capsule for dental restoration material according to the present invention will be described.

In the drawings, a numeral 1 shows integrally formed synthetic resin-made cylindrical capsule main body, in which a definite amount of a previously weighed powder component A is accommodated and which is provided with a cylindrical mixing compartment 1a for mixing the powder component A with a liquid component B when the liquid component B flows thereinto. The capsule main body 1 is also provided with an outlet hole 1b for a mixture comprising the powder component A and the liquid component B mixed with each other on a center axis in a front end portion thereof. Each of the exemplified embodiments as shown in the drawings has a shape such that a cap 4 provided with a nozzle 4a as described later on an outer surface of the front end portion, or a cap 4 supporting the nozzle 4a together with the capsule main body 1, can be fixed (a male screw in the embodiments shown in FIGS. 2 to 4 and an engagement concave in the embodiment shown in FIG. 5, respectively).

A numeral 2 shows a liquid-accommodating tool for accommodating a definite amount of the previously weighed liquid component B. In the example of the embodiment shown in FIG. 2, the liquid-accommodating tool 2 is an integrally formed synthetic resin-made cylindrical cap that can slide toward the side of the outlet hole 1b for the mixture within the cylindrical mixing compartment 1a of the capsule main body 1 and is provided with a thin film-like seal portion 2a to form a circular flow-in hole for the liquid component B on a center axis in a front end portion thereof. In the examples of the embodiments shown in FIGS. 3 and 4, the liquid-accommodating tool 2 is constituted by a bag (pillow) in which the liquid component B is wrapped by a sheet film made by a resin, a metal foil, or a laminate made by a resin and a metal foil, to be installed between the capsule main body 1 and the cap 4 provided with the nozzle 4a. In the examples of the embodiment shown in FIG. 5, the liquid-accommodating tool 2 is constituted by a bag (pillow) in which the liquid component B is wrapped by a sheet film made by a resin, a metal foil, or a laminate made by a resin and a metal foil, to be installed in the outside of an aperture hole provided on the side surface of the capsule main body 1.

Figure 2:
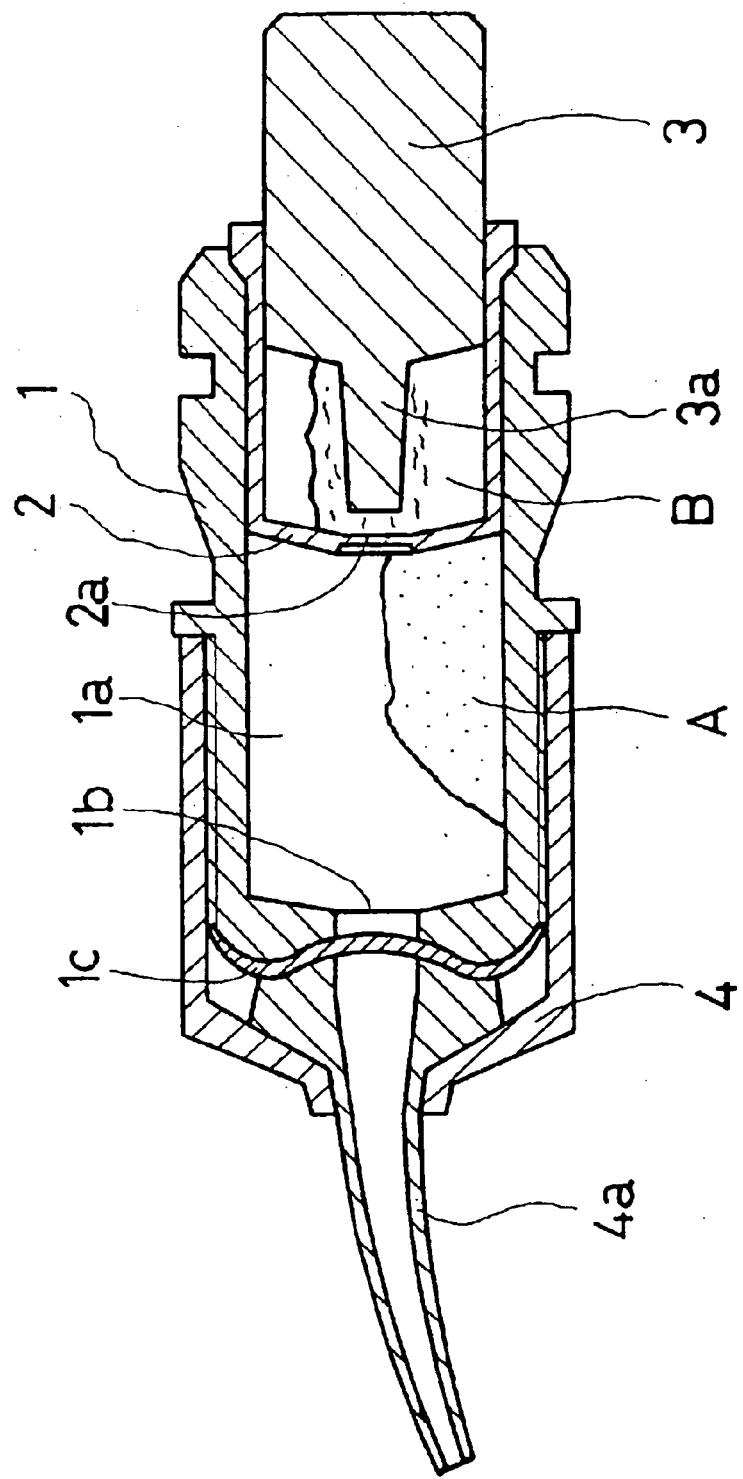
FIG. 2 is an explanatory side cross-sectional view of one embodiment of a capsule for dental restoration material used in a mixer for a capsule for dental restoration material according to the present invention.
Figure 3:
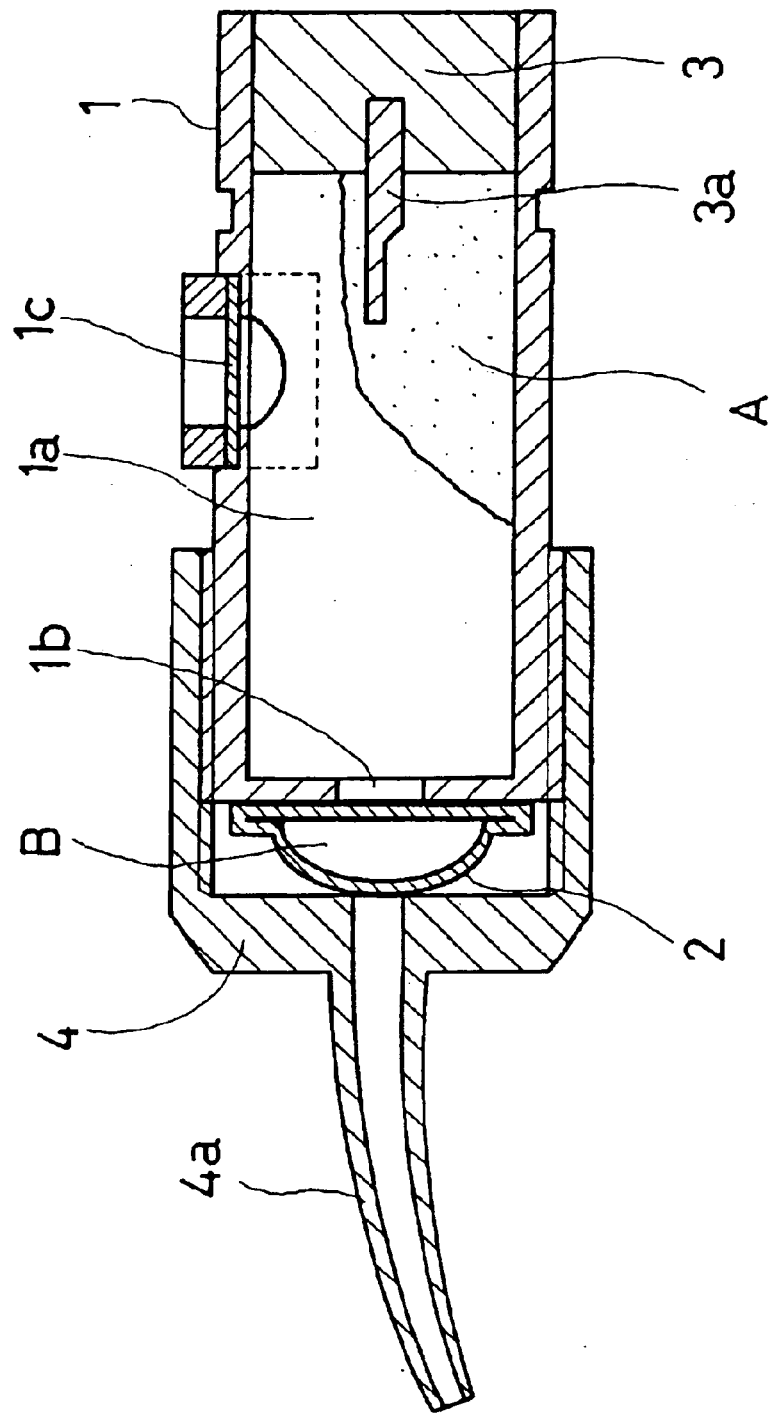
FIG. 3 is an explanatory side cross-sectional view of another embodiment of a capsule for dental restoration material used in a mixer for a capsule for dental restoration material according to the present invention.
Figure 4:
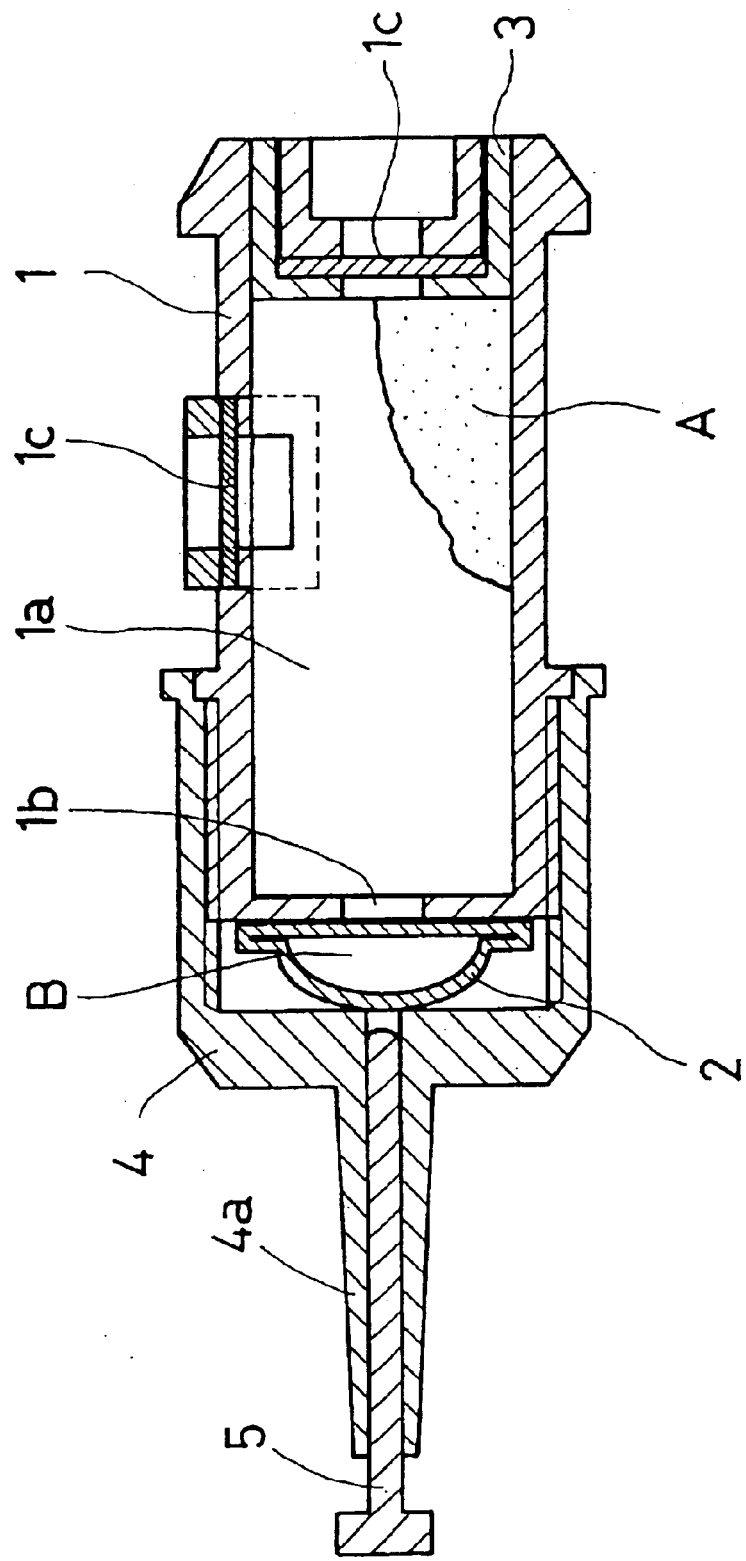
FIG. 4 is an explanatory side cross-sectional view of a still another embodiment of a capsule for dental restoration material used in a mixer for a capsule for dental restoration material according to the present invention.
Figure 5:
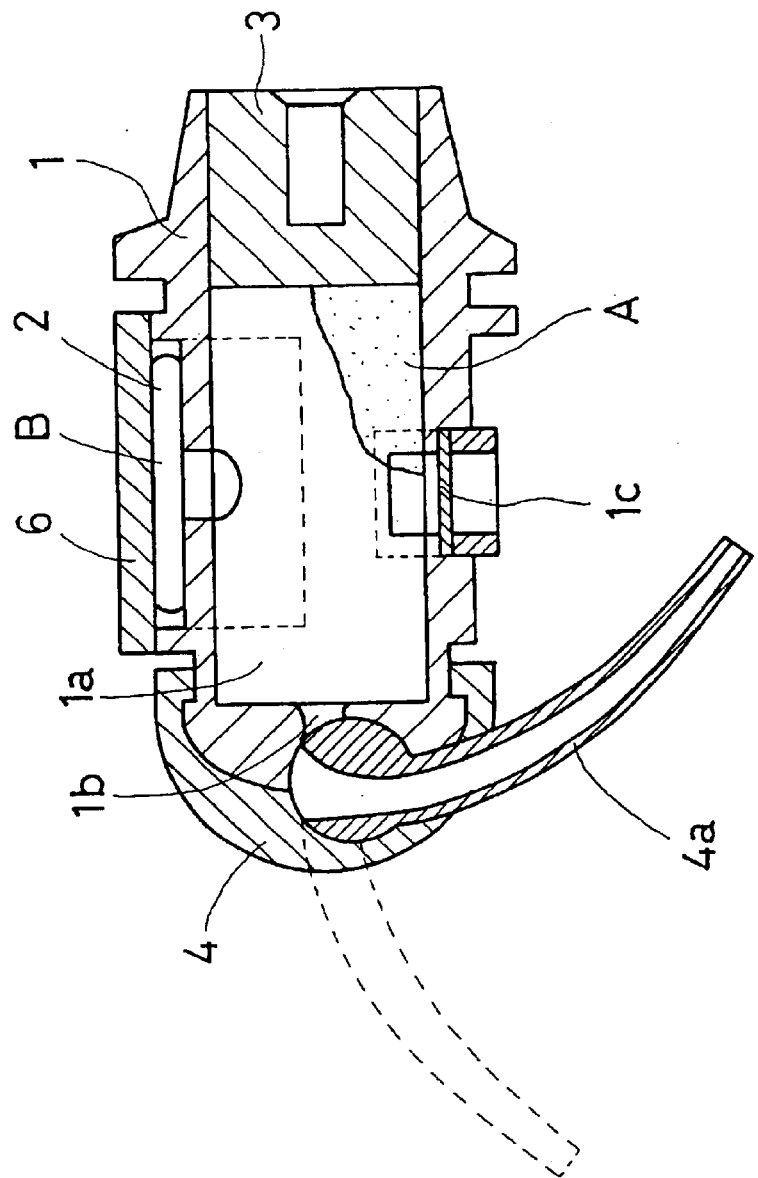
FIG. 5 is an explanatory side cross-sectional view of a still other embodiment of a capsule for dental restoration material used in a mixer for a capsule for dental restoration material according to the present invention.

A numeral 3 shows a synthetic resin-made plunger for extruding the mixture of the powder component A and the liquid component B mixed with each other within the mixing compartment 1a of the capsule main body 1 toward the side of the outlet hole 1b for the mixture. The example of the embodiment in FIG. 2 shows an embodiment in which the plunger 3 is a integrally formed synthetic resin-made one that can slide toward the side of the thin film-like seal portion 2a within the liquid-accommodating tool 2, a rod-like protrusion 3a breaking through the thin film-like seal portion 2a of the liquid-accommodating tool 2 is provided in a front end portion thereof, and after leading the liquid component B within the liquid-accommodating tool 2 to flow into the mixing compartment 1a of the capsule main body 1, the plunger 3 moves together with the liquid-accommodating tool 2, thereby inserting the rod-like protrusion 3a into the outlet hole 1b for the mixture of the capsule main body 1. The examples of the embodiments shown in FIGS. 3 to 5 show that plunger 3 is an integrally formed synthetic resin-made one having such a shape that the mixture can slide toward the side of the outlet hole 1b for the mixture within the mixing compartment 1a of the capsule main body 1. In the example of the embodiment shown in FIG. 3, the plunger 3 is provided with the rod-like protrusion 3a breaking through the sheet film on the opposite side to the outlet hole 1b of the liquid-accommodating tool 2 in the front end portion thereof.

A numeral 4 shows a synthetic resin-made cap having such a shape that it can be fixed to an outer surface of the front end portion of the capsule main body 1 for disposing the nozzle 4a in the front end portion of the capsule main body 1 (a male screw in the embodiments shown in FIGS. 2 to 4 and an engagement protrusion in the embodiment shown in FIG. 5, respectively). The cap 4 includes the embodiments shown in FIGS. 2 and 5 in which when the cap 4 is fixed to the outer surface of the front end portion of the capsule main body 1, it supports the nozzle 4a between the cap 4 and the capsule main body 1 and those shown in FIGS. 3 and 4 in which the nozzle 4a is formed integrally with the cap 4. Further, while not showing in the drawings, it is not necessary that the liquid-accommodating tool 2 is disposed facing the outlet hole 1b of the capsule main body 1, as in the embodiments shown in FIGS. 2 and 5. Moreover, there is an embodiment in which in the case where the nozzle 4a is not rotated, the cap 4 can be omitted, whereby the nozzle 4a is fixed to the capsule main body 1 by screw engagement or embedding.

In the case where the liquid-accommodating tool 2 is a capsule comprising a bag (pillow) containing the liquid component B wrapped by the sheet film as in the embodiment shown in FIG. 4, a numeral 5 shows a through rod previously set within the nozzle 4a provided on a center axis of the cap 4, such that it breaks through the sheet film on the opposite side to the outlet hole 1b of the liquid-accommodating tool 2, thereby enabling to supply the mixture of the powder component A and the liquid component B mixed within the mixing compartment 1a of the capsule main body 1 into the nozzle 4a.

In the case where the liquid-accommodating tool 2 is a capsule comprising a bag (pillow) containing the liquid component B wrapped by the sheet film as in the embodiment shown in FIG. 5, a numeral 6 shows a clip installing the liquid-accommodating tool 2 in an outer portion of the side wall of the mixing compartment 1a of the capsule main body 1. For the use, the clip 6 is pushed toward the direction of the mixing compartment 1a to smash and break the sheet film of the liquid-accommodating tool 2 having the liquid component B accommodated therein, thereby enabling to supply the liquid component B into the mixing compartment 1a of the capsule main body 1.

In the capsules for dental restoration material having such various shapes, which can be used in the mixer for a capsule for dental restoration material according to the present invention, an air-permeable filter 1c that does not pass the powder component A and the liquid component B therethrough but can ventilate air within the mixing compartment 1a into the outside of the mixing compartment 1a is placed at least in a part of a peripheral wall of the cylindrical mixing compartment 1a of the capsule main body 1.

In the embodiment shown in FIG. 2, the air-permeable filter 1c is placed in a state of clogging a mixture passage connecting the nozzle 4a for directly administering the mixture to a restoration site of a tooth to the mixing compartment 1a; in the embodiments shown in FIGS. 3 and 5, the air-permeable filter 1c is placed on the side wall of the mixing compartment 1a; and in the embodiment shown in FIG. 4, the air-permeable filter 1c is placed on the side wall of the mixing compartment 1a and the plunger 3 extruding the mixture within the mixing compartment 1a toward the nozzle 4a for directly administering it to a restoration site of a tooth. In order to fix the air-permeable filter 1c at least in a part of the peripheral wall of the cylindrical mixing compartment 1a of the capsule main body 1, it is necessary to place the air-permeable filter 1c along the peripheral wall of the cylindrical mixing compartment 1a of the capsule main body 1. Accordingly, in cases other than the case where the air-permeable filter 1c is kept between the capsule main body 1 and the cap 4 so as to clog the outlet hole 1b of the capsule main body 1 as in the embodiment shown in FIG. 2, an aperture window is formed on the side wall of the cylindrical mixing compartment 1a of the capsule main body 1 or the plunger 3 in the side facing the mixing compartment 1a, and the air-permeable filter 1c disposed in the aperture window is pressed and fixed by a presser which is similarly provided with an aperture window. In this case, it is preferred that the air-permeable filter 1c is provided in a position other than the inner side wall of the mixing compartment 1a constituting a sliding surface with the plunger 3 (the liquid-accommodating tool 2 in the example of the embodiment shown in FIG. 2) that slides and moves along an inner wall of the mixing compartment 1a.

Usually, a powder component for dental restoration material has a grain size of 50 $\mu$m or less, and a liquid component for dental restoration material has a relatively high viscosity as from 220 to 750 cP as measured under the temperature condition of 23° C. using a B type rotational viscometer. Accordingly, with respect to the air-permeable filter 1c having such a characteristic, so far as material does not pass the powder component A therethrough, neither does it inevitably pass the liquid component B therethrough. Suitable examples of such materials that can be used include fabric materials textured with fibers such as cellulose fibers, glass fibers, polyethylene fluoride fibers, silicone fibers, and silica fibers; and film-like materials made of nylon, polyester, polyethylene, polypropylene, polycarbonate, polyether sulfone, or a mixture thereof.

Next, the mixer for a capsule for dental restoration material according to the present invention, in which air present in the mixing compartment 1a for mixing the dental restoration material comprising two components of the powder component A and the liquid component B accommodated in the capsule for dental restoration material having the structure as described above is sucked out of the mixing compartment 1a to render the mixing compartment 1a in vacuo, whereby the powder component A and the liquid component B are mixed with each other by shaking, will be described with reference to FIG. 1.

A numeral 7 shows a capsule holding chamber for holding the capsule for dental restoration material having the structure as described above in a portion other than a position corresponding to the air-permeable filter 1c (in the case of the capsule for dental restoration material shown in FIG. 2, a portion not clogging the front end portion of the nozzle 4a; in the case of the capsules for dental restoration material shown in FIGS. 3 and 5, a portion not clogging the aperture portion where the air-permeable filter 1c placed on the side wall of the capsule main body 1 is exposed; and in the case of the capsule for dental restoration material shown in FIG. 4, a portion not clogging at least one of the air-permeable filter 1c placed on the side wall of the capsule main body 1 and the air-permeable filter 1c placed in the aperture window as provided in the plunger 3 on the side facing the mixing compartment 1a, respectively). This capsule holding chamber 7 has a structure such that it can clog an aperture portion 7a by a lid 7b in a sealed state, while holding the capsule for dental restoration materials.

A numeral 8 shows a mixing main body provided with a driving portion for mechanically shaking the capsule holding chamber 7. The mixing main body 8 is also provided with a motor as a driving source, a power source switch, etc. as well as a vacuum device 9 and a vacuum meter 9a. This vacuum device 9 is connected at one end to the capsule holding chamber 7 via an air hose 10 and has an inlet 11 for air from a dental unit at a second end. The vacuum device 9 may be a usual vacuum pump driven by a motor. However, when the vacuum device 9 is an ejector connected to a compressed air supply device for a dental unit, a compressed air supply device for a dental unit placed in a dental clinic can be used as a power source thereof, and the system can be made at low cost and of simple structure. Thus, the latter is preferred.

In using the mixer for a capsule for dental restoration material having such a structure according to the present invention, in order to mix the dental restoration material comprising two components of the powder component A and the liquid component B accommodated within the capsule for dental restoration material as proposed by the present inventors, it is necessary to carry out an operation in which the liquid component B within the liquid-accommodating tool 2 is led to flow into the mixing compartment 1a of the capsule main body 1. This operation is carried out in the following manner. That is, in the capsule for dental restoration material of the embodiment shown in FIG. 2, the plunger 3 is caused to slide toward the side of the outlet hole 1b of the capsule main body 1, thereby breaking through the thin film-like seal portion 2a forming the flow-in hole for the liquid component B provided on the center axis of the front end portion of the liquid-accommodating tool 2; in the capsules for dental restoration material of the embodiments shown in FIGS. 3 and 4, the capsule main body 1 is moved toward the side of the cap 4, thereby rupturing and breaking a portion of the side of the outlet hole 1b of the sheet film made by a resin, a metal foil, or a laminate made by a resin and a metal foil, of the liquid-accommodating tool 2 installed between the capsule main body 1 and the cap 4 provided with the nozzle 4a; and in the capsule for dental restoration material of the embodiment shown in FIG. 5, the sheet film made by a resin, a metal foil, or a laminate made by a resin and a metal foil, of the liquid-accommodating tool 2 installed by the clip 6 on the outside of the aperture hole provided on the side surface of the capsule main body 1 is ruptured and broken by pushing the clip 6 toward the direction of the mixing compartment 1a.

Further, in order to mix the powder component A and the liquid component B within the mixing compartment 1a of the capsule for dental restoration material, it is necessary to carry out an operation in which the capsule for dental restoration material is inserted into the capsule holding chamber 7 of the mixer for a capsule for dental restoration material according to the present invention from the aperture portion 7a and then to be held. Any of the operation for making the liquid component B within the liquid-accommodating tool 2 into the mixing compartment 1a of the capsule main body 1 and the operation for holding the capsule for dental restoration material within the capsule holding chamber 7 of the mixer for a capsule for dental restoration material according to the present invention may be carried out in advance. However, in the capsule for dental restoration material held in the capsule holding chamber 7 of the mixer for a capsule for dental restoration material, when there is no device for causing the liquid component B within the liquid-accommodating tool 2 to flow into the mixing compartment 1a of the capsule main body 1, an operation for causing the liquid component B within the liquid-accommodating tool 2 to flow into the mixing compartment 1a of the capsule main body 1 is carried out in advance.

Next, the lid 7b is closed for the capsule holding chamber 7 to be sealed. Then, air within the mixing compartment 1a is sucked out of the mixing compartment 1a via the air-permeable filter 1c placed at least in a part of the peripheral wall of the cylindrical mixing compartment 1a of the capsule main body 1 such that a pressure within the capsule holding chamber 7 which is indicated by the vacuum meter 9a reaches a prescribed degree of vacuum by the vacuum device 9. Subsequently, the driving portion of the mixing main body 8 is driven to mechanically shake the capsule holding chamber 7, thereby mixing the powder component A and the liquid component B. There is thus prepared a mixture where no air bubbles are present.

After mixing of the powder component A and the liquid component B has been completed, the vacuum of the capsule holding chamber 7 is released, the lid 7b is opened, and the capsule for dental restoration material is then taken out from the aperture portion 7a and is installed separately in an exclusive applier (not shown). Thereafter, the plunger 3 is moved toward the side of the outlet hole 1b of the capsule main body 1 by means of a push rod of the applier. At this time, in the capsule for dental restoration material of the embodiment shown in FIG. 4, a portion in the opposite side to the outlet hole 1b of the sheet film made by a resin, a metal foil, or a laminate made by a resin and a metal foil, of the liquid-accommodating tool 2 is broken through by means of the through rod 5 set within the nozzle 4a provided on the center axis of the cap 4, and the through rod 5 is then taken out from the nozzle 4a. Further, in the capsule for dental restoration material of the embodiment shown in FIG. 5, the nozzle 4a is rotated to a position shown by a broken line, thereby connecting the outlet hole 1b of the capsule main body 1 to the nozzle 4a.

Thus, when the plunger 3 is moved toward the side of the outlet hole 1b of the capsule main body 1 by pushing with the push rod of the applier, the mixture within the mixing compartment 1a of the capsule main body 1 is extruded toward the outlet hole 1b of the capsule main body 1 in a state that no air bubbles are present and administered to a restoration site of a tooth from the nozzle 4a. In this case, in the capsule for dental restoration material of the embodiment shown in FIG. 2, the rod-like protrusion 3a of the plunger 3 penetrates through the outlet hole 1b of the capsule main body 1 and breaks through the air-permeable filter 1c installed between the capsule main body 1 and the cap 4 provided with the nozzle 4a. Further, in the capsule for dental restoration material of the embodiment shown in FIG. 3, when the rod-like protrusion 3a of the plunger 3 penetrates through the outlet hole 1b of the capsule main body 1 and breaks through a portion on the opposite side to the outlet hole 1b of the sheet film made by a resin, a metal foil, or a laminate made by a resin and a metal foil, of the liquid-accommodating tool 2 installed between the capsule main body 1 and the cap 4 provided with the nozzle 4a, the mixture is administered to a restoration site of a tooth from the nozzle 4a.

As described above in detail, the mixer for a capsule for dental restoration material according to the present invention is a mixer for a capsule for dental restoration material for mixing a powder component and a liquid component of a dental restoration material by shaking within a mixing compartment of a capsule for dental restoration material having an air-permeable filter, which can ventilate air within the mixing compartment into the outside of the mixing compartment, the filter constituting as an outer wall at least a part of a peripheral wall of the mixing compartment, wherein the mixer is provided with a capsule holding chamber for holding the capsule for dental restoration material in a portion other than a portion corresponding to the air-permeable filter, and the capsule holding chamber is connected to a vacuum device. Accordingly, the mixing compartment is rendered in vacuo, and shaking is carried out to mix the powder component and the liquid component, thereby making the dental restoration material in a good state that no air bubbles are present in the mixture. Thus, the dental restoration material can be administered directly to a restoration site such as a cavity of a tooth.

Further, when, in the mixer for a capsule for dental restoration material according to the present invention, the vacuum device is an ejector to be connected to a compressed air supply device for a dental unit, a compressed air supply device for a dental unit placed in a dental clinic can be used as a power source thereof, and hence, the system can be made at low cost and of simple structure.

In the light of the above, the mixer for a capsule for dental restoration material according to the present invention, which possesses various advantages, is greatly valuable in contributing to the dental field.

While the invention has been described in detail and with reference to specific embodiments thereof, it will be apparent to one skilled in the art that various changes and modifications can be made therein without departing from the spirit and scope thereof.

What is claimed is:

1. A mixer and a capsule in combination for a dental restoration material for mixing a powder component and a liquid component of the dental restoration material by shaking, comprising:

a capsule configured to retain the dental restoration material and including a mixing compartment and an air-permeable filter configured to ventilate air within the mixing compartment to an outside of the mixing compartment, placed as an outer wall constituting at least a part of a peripheral wall of the mixing compartment, the capsule containing an outlet hole through which the dental restoration material passes;

a capsule holding chamber configured to hold the capsule in a portion other than a portion corresponding to the air-permeable filter, the capsule holding chamber being connected to a vacuum device; and a plunger including a protrusion portion configured to fit into said outlet hole of said capsule, the plunger disposed within the capsule and configured to extrude the dental restoration material when moving and inserting the protrusion portion into said outlet hole.

2. The mixer and a capsule in combination for dental restoration material as claimed in claim 1, wherein the vacuum device is an ejector connected to a compressed air supply device for a dental unit.

3. The mixer and a capsule in combination for dental restoration material as claimed in claim 1, further comprising a cap coupled to the capsule, said air-permeable filter being placed between the capsule and the cap.

4. The mixer and a capsule in combination for dental restoration material as claimed in claim 3, further comprising a nozzle extending from said capsule and having a mixture passage, said air-permeable filter being disposed within the mixture passage.

5. The mixer and a capsule in combination for dental restoration material as claimed in claim 1, further comprising an aperture window formed on the peripheral wall, said air-permeable filter being disposed in the aperture window.

6. The mixer and a capsule in combination for dental restoration material as claimed in claim 1, further comprising:

an aperture window formed on the plunger, said air-permeable filter being disposed in the aperture window.

* * * * *